United States Patent
Helmus et al.

(10) Patent No.: US 7,625,552 B2
(45) Date of Patent: Dec. 1, 2009

(54) BIOACTIVE POLYMERS FOR IMPARTING BIOACTIVE CHARACTER TO HYDROPHOBIC MEDICAL ARTICLE SURFACES

(75) Inventors: Michael N. Helmus, Worcester, MA (US); Paul Valint, Pittsford, NY (US); Shrirang V. Ranade, Arlington, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 154 days.

(21) Appl. No.: 11/442,773

(22) Filed: May 30, 2006

(65) Prior Publication Data

US 2007/0280987 A1    Dec. 6, 2007

(51) Int. Cl.
  *A61K 38/05*    (2006.01)
  *A61K 38/06*    (2006.01)
  *A61K 38/08*    (2006.01)
  *A61K 38/16*    (2006.01)
  *A61K 31/727*   (2006.01)
  *A61K 31/785*   (2006.01)
  *C08G 63/91*    (2006.01)

(52) U.S. Cl. .............. 424/78.27; 424/423; 525/54.1; 525/54.2; 514/17; 514/18; 514/56; 530/395

(58) Field of Classification Search .......... None
See application file for complete search history.

(56) References Cited

U.S. PATENT DOCUMENTS

| | | | |
|---|---|---|---|
| 4,192,783 A * | 3/1980 | Bomball et al. ........... 524/21 |
| 5,405,618 A | 4/1995 | Buttery et al. ........... 424/486 |
| 5,514,581 A * | 5/1996 | Ferrari et al. ........... 435/252.3 |
| 5,882,902 A * | 3/1999 | Nilsson ................ 435/74 |
| 5,952,398 A | 9/1999 | Dietz et al. ............ 522/184 |
| 6,156,572 A | 12/2000 | Bellamkonda et al. ..... 435/395 |
| 6,713,584 B1 | 3/2004 | Chisholm et al. ....... 526/329.7 |
| 2003/0087111 A1 | 5/2003 | Hubbell et al. ......... 428/457 |
| 2005/0187146 A1* | 8/2005 | Helmus et al. .......... 514/8 |
| 2006/0013853 A1 | 1/2006 | Richard ............... 424/423 |

OTHER PUBLICATIONS

Vulic I, Okano T, Kim SW, Synthesis and CHaracterization of Polystyrene-Poly(Ethylene Oxide)-Heparin Block Copolymers, Journal of Polymer Science: Part A: Polymer Chemistry, 1988, 26(2): 381-391.*
Slgma Catalog, p. 504.*
Definition of Chain Transfer Agent from http://composite.about.com/library/glossary/c/bldef-c1028.htm.*
Landfester, K., "Polyreactions in Miniemulsions," *Macromol. Rapid Commun*. 2001, 22, No. 12, 896-936.
Co, Carlos C. et al., "Microstructure Transformation During Microemulsion And Micellar Polymerizations," NIST Center For Neutron Research, Accomplishments and Opportunities 1998, 32-33.

* cited by examiner

*Primary Examiner*—Cecilia Tsang
*Assistant Examiner*—Julie Ha
(74) *Attorney, Agent, or Firm*—Mayer & Williams, P.C.; David B. Bonham, Esq.

(57) ABSTRACT

According to an aspect of the present invention, bioactive polymers are provided which have (a) a hydrophilic bioactive portion and (b) at least one hydrophobic polymer group that is linked to the hydrophilic bioactive portion by a covalent linkage that contains a chain transfer agent residue. According to another aspect of the present invention, medical articles are provided with bioactive surface by coating them with a coating material that contains such bioactive polymers.

20 Claims, No Drawings

US 7,625,552 B2

SEQUENCE LISTING

<160> NUMBER OF SEQ ID NOS: 2

<210> SEQ ID NO 1
<211> LENGTH: 4
<212> TYPE: PRT
<213> ORGANISM: Artificial
<220> FEATURE:
<223> OTHER INFORMATION: chemically synthesized

```
<400> SEQUENCE: 1

Arg Glu Asp Val
1

<210> SEQ ID NO 2
<211> LENGTH: 5
<212> TYPE: PRT
<213> ORGANISM: Artificial
<220> FEATURE:
<223> OTHER INFORMATION: chemically synthesized

<400> SEQUENCE: 2

Tyr Ile Gly Ser Arg
1               5
```

BIOACTIVE POLYMERS FOR IMPARTING BIOACTIVE CHARACTER TO HYDROPHOBIC MEDICAL ARTICLE SURFACES

BACKGROUND

It is sometimes desirable to coat medical articles, such as implantable and insertable medical devices, with bioactive substances such as glycosaminoglycans and peptides (including full length proteins), among others.

Bioactive substances, however, are commonly hydrophilic, whereas medical articles, including many metallic and polymeric medical articles, are hydrophobic, making it difficult to provide such medical articles with bioactive coatings.

These and other challenges are addressed by the present invention.

SUMMARY

According to an aspect of the present invention, bioactive polymers are provided, which comprise (a) a hydrophilic bioactive portion and (b) a hydrophobic polymer group that is linked to the hydrophilic bioactive portion by a covalent linkage that comprises a chain transfer agent residue.

Such bioactive polymers are advantageous in that they may be used to coat hydrophobic medical article surfaces, thereby rendering the medical article surfaces bioactive.

These and other aspects, embodiments and potential advantages of the present invention will become immediately apparent to those of ordinary skill in the art upon reading the Detailed Description to follow.

DETAILED DESCRIPTION

In the present invention hydrophilic bioactive species are rendered compatible with hydrophobic surfaces via a hydrophobic polymer group.

According to an aspect of the present invention, bioactive polymers are provided, which contains the following: (a) a hydrophilic bioactive portion and (b) at least one hydrophobic polymer group linked to the hydrophilic bioactive portion by a covalent linkage that comprises a chain transfer agent residue.

According to another aspect the present invention, medical articles are provided, which contain a hydrophobic material surface and a coating disposed on the surface which comprises bioactive polymers like those above.

As used herein, a "bioactive species" is a species that promotes adhesion with adjacent tissue, for example, bone tissue or soft tissue, with minimal adverse biological effects (e.g., the formation of connective tissue such as fibrous connective tissue).

Examples of hydrophilic bioactive species suitable for the practice of the present invention include adhesive polysaccharide-containing species and adhesive peptide-containing species (including cell adhesive peptides and full-length proteins) among others. Such species may be selected, for example, from the following: (a) extracellular materials such as submucosa, bone marrow, extracellular membrane, ECM, and basement membrane, various components of extracellular materials, including fibrous materials and ground substance (e.g., glycosaminoglycans, proteoglycans, and glycoproteins), for instance, collagen, laminin, elastin, fibronectin, heparin, heparin sulfate, hyaluron, dermatan sulfate, keratin sulfate, and chrondroitin sulfate, among others; (b) adhesive species such as ankyrins, cadherins (calcium dependent adhesion molecules), N-CAMs (calcium independent adhesive molecules), connexins, immunoglobulins, mucoadhesives, sialyl Lex, plant or bacterial lectins (adhesion molecules which specifically bind to sugar moieties of the epithelial cell membrane), integrins, entactin, fibrin, vimentin, glycolipids, glycophorin, glycoproteins, hyaluronic acid, spektrin, von Willebrand factor, vinculin, vitronectin, and polypeptides and proteins containing cell adhesion peptides such as RGD tripeptide (i.e., ArgGlyAsp, which has been identified to be responsible for some of the cell adhesion properties of fibronectin, laminin, collagen I, collagen IV, thrombospondin, and tenascin), REDV tetrapeptide (i.e., Arg-Glu-Asp-Val), which has been shown to support endothelial cell adhesion but not that of smooth muscle cells, fibroblasts, or platelets, and YIGSR pentapeptide (i.e., TyrIleGlySerArg), which promotes epithelial cell attachment, but not platelet adhesion); and (c) growth factors. More information on RGD, REDV, and YIGSR peptides can be found in U.S. Pat. No. 6,156,572 and U.S. Patent Application No. 2003/0087111.

As used herein, "polymers" are molecules containing multiple copies (typically on the order of 5 to 10 to 50 to 100 to 500 to 1000 or more copies) of one or more types of constitutional units, commonly referred to as monomers. As used herein, "homopolymers" are polymers that contain multiple copies of a single type of constitutional unit. "Copolymers" are polymers that contain multiple copies of at least two dissimilar constitutional units.

A "polymeric material" is one that contains polymers, for example, 50 to 75 to 90 to 95 to 99 wt % or more polymers.

As used herein, a "polymer group" is a grouping of constitutional units (monomers), for example, containing 5 to 10 to 50 to 100 to 500 to 1000 or more units. Polymer groups can contain a single type of constitutional unit (also referred to herein as "homopolymeric groups") or multiple types of constitutional units (also referred to herein as "copolymeric groups") which may be provided, for example, in a random, statistical, gradient, or periodic (e.g., alternating) distribution. Polymer groups for use in the present invention may have a variety of architectures, including linear and branched architectures. Branched architectures include star-shaped architectures (e.g., architectures in which three or more chains emanate from a single branch point), comb architectures (e.g., architectures having a main chain and a plurality of side chains) and dendritic architectures (e.g., arborescent and hyperbranched polymers), among others. As used herein a "polymer chain" is a linear (unbranched) grouping of constitutional units.

Examples of hydrophobic polymer groups include homopolymer groups and copolymer groups formed from suitable members (e.g., those polymerizable by free radical techniques) selected from the following: (1) vinyl aromatic monomers including (a) unsubstituted vinyl aromatic monomers, such as styrene and 2-vinyl naphthalene, (b) vinyl substituted aromatic monomers such as α-methyl styrene, (c) ring-substituted vinyl aromatic monomers including (i) ring-alkylated vinyl aromatic monomers such as 3-methylsytrene, 4-methylsytrene, 2,4-dimethylsytrene, 2,5-dimethylsytrene, 3,5-dimethylsytrene, 2,4,6-trimethylsytrene, and 4-tert-butylstyrene, (ii) ring-alkoxylated vinyl aromatic monomers, such as 4-methoxysytrene and 4-ethoxysytrene, (iii) ring-halogenated vinyl aromatic monomers such as 2-chlorosytrene, 3-chlorosytrene, 4-chlorosytrene, 2,6-dichlorosytrene, 4-bromostyrene and 4-fluorostyrene, and (iv) ester-substituted vinyl aromatic monomers such as 4-acetoxysytrene; (2) other vinyl monomers including (a) vinyl ester monomers such as vinyl acetate, vinyl propionate, vinyl benzoate, vinyl 4-tert-butyl benzoate, vinyl cyclohexanoate, vinyl pivalate, vinyl trifluoroacetate, vinyl butyral, (b) vinyl halide monomers such as vinyl chloride and vinyl fluoride; (c) alkyl vinyl ether monomers such as propyl vinyl ether, butyl vinyl ether, isobutyl vinyl ether, tert-butyl vinyl ether, cyclohexyl vinyl ether, 2-ethylhexyl vinyl ether and dodecyl vinyl ether, and (d) other vinyl monomers such as 1-vinyl-2-pyrrolidone and vinyl ferrocene, (3) certain acrylic acid derivatives, for example, (a) alkyl acrylate monomers such as isopropyl acrylate, butyl acrylate, sec-butyl acrylate, isobutyl acrylate, cyclohexyl acrylate, tert-butyl acrylate, hexyl acrylate, 2-ethylhexyl acrylate, dodecyl acrylate, hexadecyl acrylate, and isobornyl acrylate, (b) arylalkyl acrylate monomers such as benzyl acrylate, (c) alkoxyalkyl acrylate monomers such as 2-ethoxyethyl acrylate and 2-methoxyethyl acrylate, (d) haloalkyl acrylate monomers such as 2,2,2-trifluoroethyl acrylate, (e) cyano-alkyl acrylate monomers such as 2-cyanoethyl acrylate; and (e) other acrylic-acid derivatives including acrylonitrile, (4) certain methacrylic acid derivatives including, for example, (a) alkyl methacrylate monomers such as methyl methacrylate, ethyl methacrylate, isopropyl methacrylate, isobutyl methacrylate, t-butyl methacrylate, cyclohexyl methacrylate, 2-ethylhexyl methacrylate, octyl methacrylate, dodecyl methacrylate, hexadecyl methacrylate and octadecyl methacrylate (b) aromatic methacrylate monomers such as phenyl methacrylate and including aromatic alkyl methacrylates such as benzyl methacrylate, (c) aminoalkyl methacrylates such as diethylaminoethyl methacrylate and 2-tert-butyl-aminoethyl methacrylate, (d) additional methacrylate monomers including isobornyl methacrylate and trimethylsilyl methacrylate, and (e) other methacrylic-acid derivatives including methacrylonitrile, (5) unsaturated hydrocarbon monomers including ethylene, propylene, isobutylene, 1-butene, 4-methyl pentene, 1-octene and other α-olefins, isoprene and butadiene; (6) halogenated unsaturated hydrocarbon monomers including tetrafluoroethylene, vinylidene chloride, vinylidene fluoride, cis-chlorobutadiene, trans-chlorobutadiene, (7) cyclic ether monomers including tetrahydrofuran, trimethylene oxide, propylene oxide, methyl glycidyl ether, butyl glycidyl ether, allyl glycidyl ether, epibromohydrin, epichlorohydrin, 1,2-epoxybutane, 1,2-epoxyoctane and 1,2-epoxydecane, and (8) combinations of the forgoing.

Further examples of hydrophobic polymer groups include biodegradable homopolymer groups and copolymer groups, for example, poly ester-amides, poly ortho-esters and polyesters based on amino acids such as lysine, leucine and tyrosine, as well as polyester polymers and copolymers such as such as polycaprolactones, poly lactic acid, poly galactic acid, and polyanhydrides, among others.

A method of making bioactive polymers in accordance with the present invention will now be described, in accordance with an embodiment of the invention. As a first step one or more chemical groups that act as chain transfer agents (CTAs) during the course of free radical polymerization reactions are linked to the hydrophilic bioactive species (or stated another way, the hydrophilic bioactive species are functionalized with the CTAs).

CTAs readily enter into free radical polymerization reactions due to the high reactivity between radical species and the CTA. The number of CTAs that may be linked to the bioactive species ranges from one to many CTAs, but, in general, not so many that the activity of the resulting species (i.e., the bioactive polymer) is significantly compromised. The bioactive species with the one or more linked CTAs is referred to herein as a bioactive CTA.

Examples of CTAs are mercaptans or thiols and alkyl halides among others.

More preferred are monofunctional and polyfunctional thiols, including alkyl thioglycollates such as 2-ethyl hexyl thioglycollate or octyl thioglycollate, mercaptoethanol, mercaptopropyltrimethoxysilane, 3-mercapto-1-propanol, 3-mercapto-2-butanol, 11-mercapto-1-undecanol, 1-mercapto-2-propanol, 2-mercaptoethanol, 2-aminoethanethiol, 6-mercapto-1-hexanol, 2-mercaptobenzyl alcohol, 3-mercapto-1,2-propanediol, 4-mercapto-1-butanol, thiosalicylic acid, mercaptoacetic acid, mercaptoundecanoic acid, thiolactic acid, thiobutyric acid, thioglycollic acid, mercaptopropionic acid, mercaptosuccinic acid, 2-mercaptobenzothiazole, 2-mercaptobenzoxazole, 2-mercaptobenzimidazole, trimethylol propane tris(3-mercaptopropionate), pentaerythritol tetra(3-mercaptopropionate), pentaerythritol tetrathioglycollate, pentaerythritol tetrathiolactate, pentaerythritol tetrathiobutyrate, dipentaerythritol hexa(3-mercaptopropionate), dipentaerythritol hexathioglycollate, tripentaerythritol octa(3-mercaptopropionate), and tripentaerythritol octathioglycollate, among others.

The particular choice of chain transfer agent will depend in many cases upon the ease with which it may be attached to the bioactive species. In this regard, one particularly beneficial group of CTAs are those that contain amino groups, for example, aminoalkylthiols such as 2-aminoethanethiol. Because they contain amine groups, they can participate in carbodiimide coupling with bioactive species containing one or more carboxyl groups, for example, glycosaminoglycans and peptides containing acidic amino acids (e.g., glutamic acid and aspartic acid), among others.

Conversely, another beneficial group of CTAs are those that contain carboxyl groups such as thiosalicylic acid, mercaptoacetic acid, mercaptoundecanoic acid, thiolactic acid, thiobutyric acid, thioglycollic acid, mercaptopropionic acid, mercaptosuccinic acid, and so forth. Because these CTAs contain carboxylic acid groups, they can participate in carbodiimide coupling with bioactive species containing one or more amino groups, for example, peptides containing basic amino acids (e.g., arginine, lysine, and histidine), among others.

Carbodiimide couple agents are well known and include, for example, 1-alkyl-3-(3-dimethylaminopropyl) carbodiimides such as 1-ethyl-3-(3-dimethylaminopropyl)carbodiimide hydrochloride (EDC), 1-benzyl-3-(3-dimethylaminopropyl)carbodiimide (BDC), 1-cyclohexyl-3-(2-morpholinyl-4-ethyl)carbodiimide (CMC), and 1,3-dicyclohexylcarbodiimide (DCC). In some instances, supplemental agents may optionally be added to enhance the coupling reaction, including, for example, N-hydroxysuccinimide, among others.

Also a bioactive agent that contains a peptide chain can be the CTA, if the peptide has one or more thiol containing amino acids such as cysteine.

As noted above, CTAs readily enter into free radical polymerization reactions due to the high reactivity between radical species and the CTAs. Once a radical species has been transferred to the CTA, polymer chain formation initiates readily at the CTA. Thus, as a general rule, the polymer that forms in the presence of the CTA has the CTA incorporated into the polymer as one of its end groups. For example, a thiol CTA, RSH, where R is an organic species, added to a polymerization reaction would yield a polymer with a sulfide group at one end of the polymer and a hydrogen at the other end.

In the present invention, the CTA residue will act as a link between the bioactive species and the polymer that is formed. For instance, where a mercaptan or thiol CTA is employed, the linkage will comprise an —S— linkage.

It is somewhat challenging to polymerize a hydrophobic monomer, which is not water soluble, from the bioactive CTAs of the invention, which are water soluble and thus incompatible with the monomer. This incompatibility may be overcome by using an emulsion polymerization process or a micellar polymerization process, for example, micellar chain transfer polymerization, MCTP. In MCTP, an aqueous phase that contains the bioactive CTA is dispersed within micelles in a nonaqueous, or oil, phase, or vice versa. Examples of oil phase materials include hydrophobic monomers such as those described herein, and may further include an optional hydrophobic solvent species such as heptane, decane, decalin, toluene, and xylene, among others. The dispersion is generally transparent because the micelle diameter is smaller than the wavelength of visible light (i.e., <400 nm).

The dispersion may be made thermodynamically stable through the use of one or more surfactants. The one or more surfactants used to stabilize the micellar dispersion are low HLB (Hydrophilic Lipophilic Balance) type surfactants, typically having HLB values ranging from 4 to 8 which are known in the art. Such surfactants may be anionic, cationic or nonionic, for example, sodium di-alkyl sulfosuccinates (e.g. sodium di-(2-ethylhexyl)sulfosuccinate, available as Aerosol OT from American Cyanamid Company, Bridgewater, N.J., USA), sorbitan monooleate (SPAN 80), sorbitan trioleate, polyoxyethylene (20) sorbitan triolate, oleamidopropyldimethylamine, polyoxyethylene sorbitol hexaoleate, sodium isostearyl-2-lactate, and the like. Once a suitable surfactant is provided in an appropriate concentration, the micelles will tend to form spontaneously with little need for vigorous mixing.

As noted above, the oil phase contains one or more types of hydrophobic monomers, selected, for example, from those listed above (e.g., styrene, butadiene, and n-butyl methacrylate, among others) and one or more oil soluble free radical initiators. Alternatively, a water soluble initiator may be provided in the aqueous phase, if desired.

Suitable oil-soluble photoinitiators are known and include those which generate free radicals upon exposure to electromagnetic radiation (e.g., ultraviolet radiation) and include benzoin and its derivatives (e.g., benzoin methyl ether, BME), benzyl, benzophenones, Michler's ketone, acetophenone derivatives, anthraquinones, and mixtures thereof, among many others. For example, there is a host of photoinitiators available from Ciba-Geigy (Novartis) within the IRGACURE and/or DARACURE initiator families.

Suitable oil-soluble thermal initiators are also known and include those which, on exposure to heat, generate free radicals, for example, azo compounds (such as 2,2'-azobisisobutyronitrile (AIBN), available from Sigma-Aldrich, USA, Charkit Chemical Corporation, USA, and SAS Chemicals, India) and various peroxides.

Medical articles include implantable or insertable medical devices upon which bioactive coatings may be applied including, for example, stents (including coronary vascular stents, peripheral vascular stents such as cerebral stents, urethral, ureteral, biliary, tracheal, gastrointestinal and esophageal stents), stent grafts, vascular grafts, catheters (e.g., renal or vascular catheters including balloon catheters), guide wires, balloons, filters (e.g., vena cava filters), vascular access ports, embolization devices including cerebral aneurysm filler coils (including Guglilmi detachable coils and metal coils), myocardial plugs, septal defect closure devices, patches, pacemakers and pacemaker leads, defibrillation leads and coils, heart valves, vascular valves, tissue engineering scaffolds for cartilage, bone, skin and other in vivo tissue regeneration, as well as other devices that are implanted or inserted into the body. The medical devices of the invention may be drug eluting (e.g., a drug eluting stent among many other possibilities).

The medical articles may have, for example, hydrophobic metallic surfaces or hydrophobic polymeric surfaces.

Specific examples of metallic materials may be selected, for example, from hydrophobic members of the following: substantially pure metals (e.g., biostable metals such as gold, platinum group metals (platinum, ruthenium, palladium, osmium, rhodium, iridium), titanium, tantalum, tungsten, and, and bioresorbable metals (e.g., magnesium and iron), metal alloys comprising iron and chromium (e.g., stainless steels, including platinum-enriched radiopaque stainless steel), alloys comprising nickel and titanium (e.g., Nitinol), alloys comprising cobalt and chromium, including alloys that comprise cobalt, chromium and iron (e.g., elgiloy alloys), alloys comprising nickel, cobalt and chromium (e.g., MP 35N) and alloys comprising cobalt, chromium, tungsten and nickel (e.g., L605), alloys comprising nickel and chromium (e.g., inconel alloys), and bioresorbable metal alloys such as magnesium alloys and iron alloys (including their combinations with Ce, Ca, Zn, Zr and Li), among many others. In this regard, noble metals and metal alloys such as gold, silver, platinum and so forth are typically hydrophobic. Other less noble metals and alloys may be more hydrophilic due to a native oxide based passive layer that forms.

Specific examples hydrophobic polymers may be selected, for example, from polymers and copolymers of one or more of the hydrophobic monomers listed above. In certain embodiments, compatibility between the bioactive polymer and a polymeric medical article surface may be enhanced by matching the monomers within each.

Although various embodiments of the invention are specifically illustrated and described herein, it will be appreciated that modifications and variations of the present invention are covered by the above teachings without departing from the spirit and intended scope of the invention.

What is claimed is:

1. A bioactive polymer comprising (a) a cell adhesion peptide comprising an amino acid sequence selected from RGD, REDV (SEQ ID NO: 1), and YIGSR (SEQ ID NO: 2) and (b) a hydrophobic polymer group comprising a monomer selected from vinyl aromatic monomers, vinyl ester monomers, vinyl halide monomers, alkyl vinyl ether monomers, alkyl acrylate monomers, alkyl methacrylate monomers, unsaturated hydrocarbon monomers, halogenated unsaturated hydrocarbon monomers, cyclic ether monomers, and combinations of the same, wherein the hydrophobic polymer group is linked to the cell adhesion peptide by a covalent linkage that comprises a thiol chain transfer agent residue comprising an —S— linkage.

2. The bioactive polymer of claim 1, wherein said hydrophobic polymer group comprises a monomer selected from styrene, butadiene, n-butyl methacrylate, and combinations of the same.

3. The bioactive polymer of claim 1, wherein said chain transfer agent residue is a residue of an aminoalkylthiol compound.

4. The bioactive polymer of claim 3, wherein said aminoalkylthiol compound is 2-aminoethanethiol.

5. The bioactive polymer of claim 1, wherein said chain transfer agent residue is a residue of a carboxyalkylthiol.

6. The bioactive polymer of claim 1, comprising a plurality of said hydrophobic polymer groups.

7. A medical article comprising a hydrophobic material surface and having a coating on said surface that comprises the bioactive polymer of claim 1.

8. The medical article of claim 7, wherein said hydrophobic material is a metallic material.

9. The medical article of claim 8, wherein said metallic material selected from gold, titanium, platinum group metals, metal alloys comprising iron and chromium, alloys comprising nickel and titanium, alloys comprising cobalt and chromium, and alloys comprising nickel and chromium.

10. The medical article of claim 8, wherein said metallic material selected from bioresorbable metals and bioresorbable metal alloys.

11. The medical article of claim 7, wherein said hydrophobic material is a hydrophobic polymeric material.

12. The medical article of claim 11, wherein said hydrophobic polymeric material comprises a monomer selected from styrene, butadiene, n-butyl methacrylate, and combinations thereof.

13. The medical article of claim 7, wherein said medical article is a stent.

14. A method of making the bioactive polymer of claim 1 comprising: (a) reacting a chain transfer agent with said cell adhesion peptide to form a bioactive chain transfer agent, (b) polymerizing said hydrophobic polymer group from said bioactive chain transfer agent, thereby forming said bioactive polymer.

15. The method of claim 14, wherein said polymerization step is micellar chain transfer polymerization step.

16. The bioactive polymer of claim 1, wherein the hydrophobic polymer group is linked to the hydrophilic bioactive portion by a covalent linkage that consists essentially of a chain transfer agent residue.

17. The bioactive polymer of claim 1, wherein said cell adhesion peptide is RGD.

18. The bioactive polymer of claim 1, wherein said cell adhesion peptide is REDV (SEQ ID NO: 1).

19. The bioactive polymer of claim 1, wherein said cell adhesion peptide is YIGSR (SEQ ID NO: 2).

20. The bioactive polymer of claim 1, wherein said bioactive polymer is formed by a method comprising: (a) reacting a chain transfer agent with said cell adhesion peptide to form a bioactive chain transfer agent, (b) polymerizing said hydrophobic polymer group from said bioactive chain transfer agent, thereby forming said bioactive polymer.

* * * * *

UNITED STATES PATENT AND TRADEMARK OFFICE
CERTIFICATE OF CORRECTION

PATENT NO. : 7,625,552 B2  
APPLICATION NO. : 11/442773  
DATED : December 1, 2009  
INVENTOR(S) : Michael N. Helmus et al.

Page 1 of 1

It is certified that error appears in the above-identified patent and that said Letters Patent is hereby corrected as shown below:

Col. 2, lines 56-63 change "3-methylsytrene, 4-methylsytrene, 2,4-dimethylsytrene, 2,5-dimethylsytrene, 3,5-dimethylsytrene, 2,4,6-trimethylsytrene, and 4-tert-butylstyrene, (ii) ring-alkoxylated vinyl aromatic monomers, such as 4-methoxysytrene and 4-ethoxysytrene, (iii) ring-halogenated vinyl aromatic monomers such as 2-chlorosytrene, 3-chlorosytrene, 4-chlorosytrene, 2,6-dichlorosytrene" to -- 3-methylstyrene, 4-methylstyrene, 2,4-dimethylstyrene, 2,5-dimethylstyrene, 3,5-dimethylstyrene, 2,4,6-trimethylstyrene, and 4-tertbutylstyrene, (ii) ring-alkoxylated vinyl aromatic monomers, such as 4-methoxystyrene and 4-ethoxystyrene, (iii) ring-halogenated vinyl aromatic monomers such as 2-chlorostyrene, 3-chlorostyrene, 4-chlorostyrene, 2,6-dichlorostyrene --.

Col. 3, line 48, after "as", delete "such as".

Col. 6, lines 26, after "and", delete "and".

Signed and Sealed this

Sixteenth Day of February, 2010

David J. Kappos  
*Director of the United States Patent and Trademark Office*